United States Patent [19]

McCammon et al.

[11] Patent Number: 5,187,850

[45] Date of Patent: Feb. 23, 1993

[54] NEEDLE DISPOSAL SYSTEM

[76] Inventors: John W. McCammon, 104 Killinchy Rd., Comber BT23 5NE; Trever L. Moffet, 106 Donaghadee Rd., Newtownards, County Down BT 23 3QP, both of Northern Ireland

[21] Appl. No.: 892,711

[22] Filed: May 29, 1992

Related U.S. Application Data

[63] Continuation of Ser. No. 630,798, Dec. 24, 1990, abandoned, which is a continuation of Ser. No. 306,017, Apr. 22, 1988, abandoned.

[30] Foreign Application Priority Data

Apr. 22, 1987 [GB] United Kingdom ............... 8709453

[51] Int. Cl.5 ............................................. B65F 1/08
[52] U.S. Cl. ........................................ 29/235; 206/366; 604/110
[58] Field of Search ................. 225/93; 206/365, 366; 29/235, 240; 604/110; 30/131

[56] References Cited

U.S. PATENT DOCUMENTS

| 3,914,865 | 10/1975 | Oakes | 30/131 |
|---|---|---|---|
| 4,035,911 | 7/1977 | Nethercutt et al. | 30/131 |
| 4,485,918 | 12/1984 | Mayer | 206/366 |
| 4,488,643 | 12/1984 | Pepper | 225/93 |
| 4,494,652 | 1/1985 | Nelson et al. | 206/366 |
| 4,520,926 | 6/1985 | Nelson | 206/366 |
| 4,565,311 | 1/1986 | Pugliese et al. | 225/94 |
| 4,576,281 | 3/1986 | Kirksey | 206/370 |
| 4,883,173 | 11/1989 | Goldman et al. | 206/366 |
| 4,892,525 | 1/1990 | Hermann, Jr. et al. | 206/365 |
| 4,956,907 | 9/1990 | Bruno | 29/235 |

FOREIGN PATENT DOCUMENTS

| 2740335 | 3/1979 | Fed. Rep. of Germany | 206/366 |
|---|---|---|---|
| 2586566 | 3/1987 | France . | |
| 2586568 | 3/1987 | France . | |
| 2603872 | 3/1988 | France | 206/366 |

Primary Examiner—Hien H. Phan
Attorney, Agent, or Firm—Nikaido, Marmelstein, Murray & Oram

[57] ABSTRACT

A needle disposal system comprises a hand held assembly of three components, namely a disposable container (10) having an inlet in its top face, a head unit (12) securable over the container (10) and a first cap (16) securable over the head unit (12). The head unit has an aperture alignable with the inlet and through which used needles (18) can be fed into the container (10) for non-returnable passage therefrom. The first cap (16) has an aperture (22) alignable with the aperture of the head unit. The cap (16) has an inverted skirt (32) extending outwardly and upwardly to act as a protective shroud to protect a hand when holding the assembly during a needle inserting operation.

17 Claims, 3 Drawing Sheets

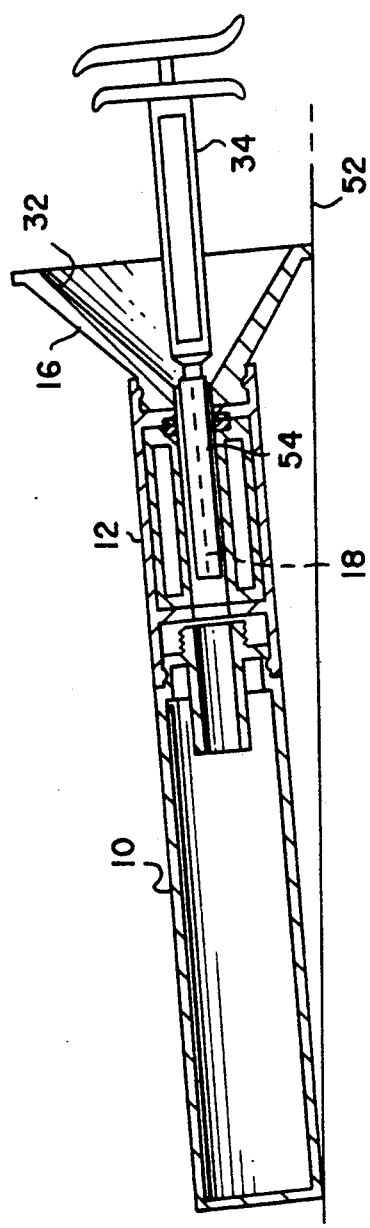
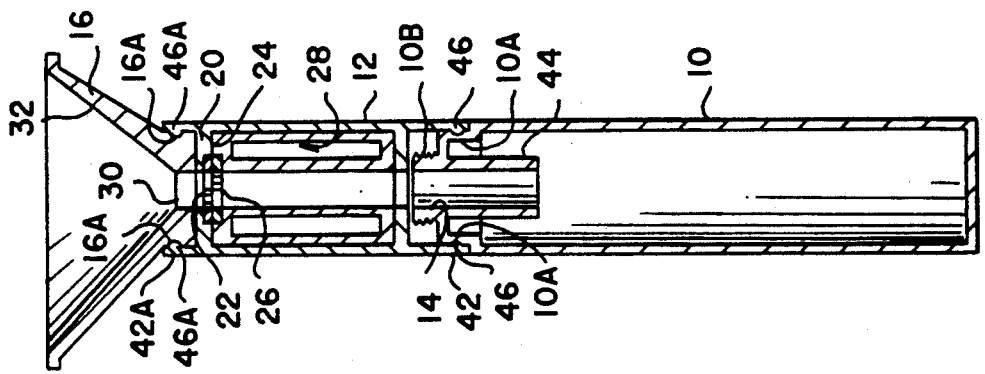
Fig.7
Fig.4

NEEDLE DISPOSAL SYSTEM

This application is a continuation of application Ser. No. 630,798, filed on Dec. 24, 1990, now abandoned, which is a continuation of application Ser. No. 306,017 filed Apr. 22, 1988, now abandoned.

FIELD OF THE INVENTION

This invention relates to a needle disposal system for use in disposing of used hypodermic needles from syringes in a manner to reduce or avoid the danger of any infection, such as hepititis or aids, being transmitted.

SUMMARY OF THE INVENTION

According to a first aspect of the present invention, a needle disposal system comprises an assembly of a disposable container having an inlet in its top face, the assembly being adapted to be hand held, and a first cap securable over the container with an aperture alignable with the inlet, and through which aperture and inlet used needles can be fed into the container for non-returnable passage therefrom, the first cap having an inverted skirt extending outwardly and upwardly to act as a protective shroud to protect a hand when holding the assembly during a needle inserting operation.

Preferably, a peripheral flange is provided extending from the outer edge of the skirt of the first cap in an outwardly and downwardly manner a distance substantially the same as the depth of the skirt.

Preferably also, the aperture in the first cap is of a shape to allow passage therethrough of a needle and has a width restriction whereby the top of a hub of a needle, located through the aperture, can be engaged under the sides defining the restriction and by pulling outwardly, the needle can be detached from a syringe.

According to a second aspect of the present invention, a needle disposal system comprises an assembly of a disposable container having an inlet in its top face, a head unit securable over the container, the assembly being adapted to be hand held, the head unit having aperture means alignable with the inlet and through which used needles can be fed into the container for non-returnable passage therefrom, and a first cap securable over the head unit with an aperture alignable with an aperture in the aperture means, the cap having an inverted skirt extending outwardly and upwardly to act as a protective shroud to protect a hand when holding the assembly during a needle inserting operation.

The container is preferably of a material resistant to passage therethrough of a needle. The head unit is beneficially reusable and of a material capable of being autoclaved.

A second cap in the form of a closure is also preferably provided to be securable over the container after the head unit and/or first cap is removed.

Preferably further, the aperture means of the head unit incorporates a valve device. The valve device preferably comprises a plate constrained to move between two extreme positions to respectively close off an aperture in a top plate of the head unit and to open the aperture. The plate is preferably spring-biased to the closed position. The movement of the plate is controlled by a trigger mechanism.

DESCRIPTION OF THE DRAWINGS

Embodiments of the present invention will now be described, by way of example, with reference to the accompanying schematic drawings, in which:

FIG. 4 is a vertical cross-sectional view of the system shown in FIG. 1 through its transverse axis;

FIG. 7 is a similar view of a needle disposal system as shown in FIG. 4 with a syringe and needle located therein and located in a reclined rest position;

DESCRIPTION OF THE PREFERRED EMBODIMENTS

Figure 1:
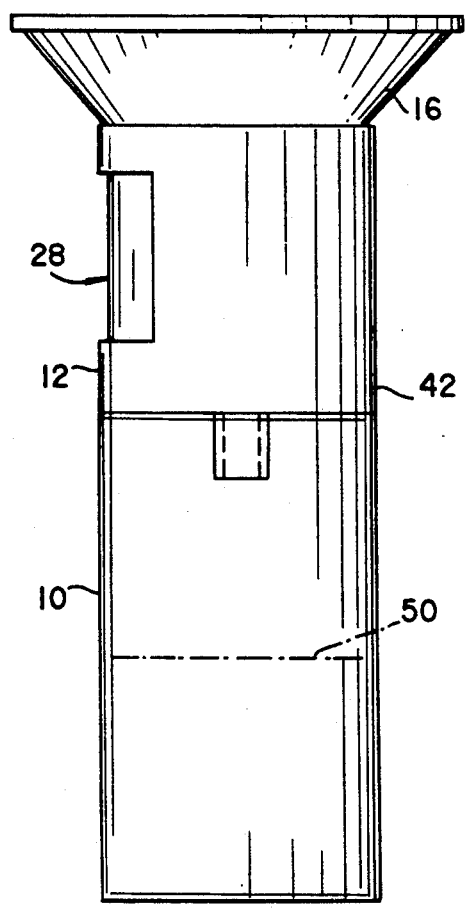
FIG. 1 is a side view of a needle disposal system according to a preferred embodiment of the present invention.

Referring to FIGS. 1 to 6 of the drawings, a needle disposal system according to a preferred embodiment comprises an assembly adapted to be hand held in an upright manner and in which position the assembly will hereinafter be described. The assembly is of a disposable container 10 having an inlet in its top face and a head unit 12 securable over said top face. The container 10 and head unit 12 have a similar oblong horizontal cross-section. The container 10 has an external screw-thread 10B around a neck 14 of its inlet which stands proud of its top face as shown and the head unit 12 has a depending surround 42 shaped as an extension of the container as shown in FIGS. 4, 5, 6 and 7. Adjacent to the bottom edge of the surround 42 on each lateral side thereof, an elongate protuberance 46 is provided to engage in a complementary groove 10A around the lateral sides of the container 10 as shown in FIG. 4 to secure the container 10 and head unit 12 together. A similar surround 42A extends upwardly and on each lateral side an elongate protuberance 46A is provided for a purpose to be described hereinafter.

Figure 5:
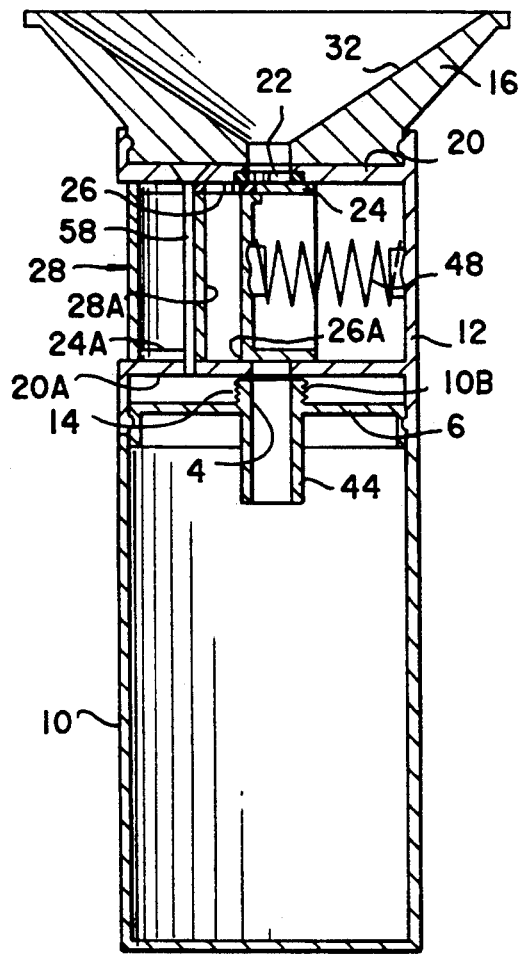
FIG. 5 is a vertical cross-sectional view of the system through its longitudinal axis with the trigger mechanism shown in a closed position.
Figure 6:
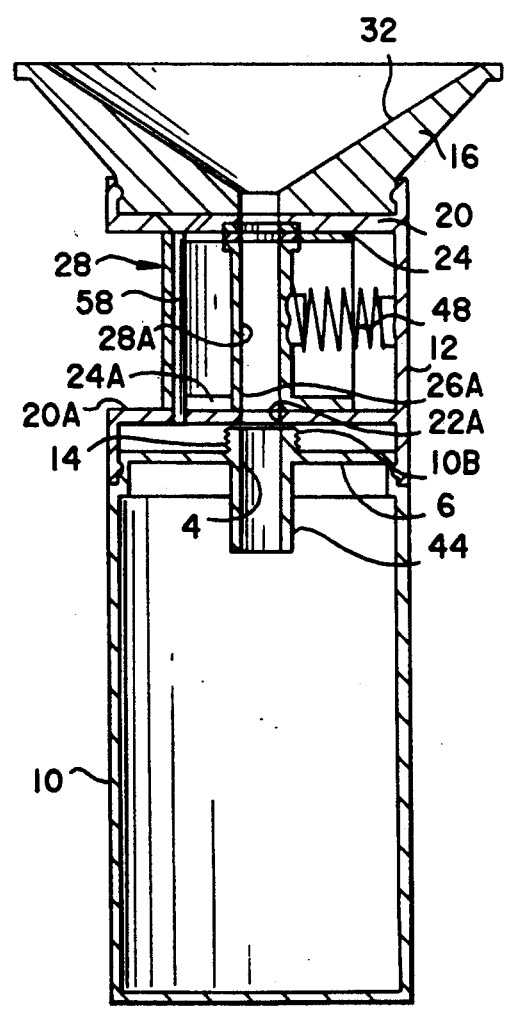
FIG. 6 is a vertical cross-sectional view of the system through its longitudinal axis with the trigger mechanism shown in a compressed open position.

The head unit 12 has aperture mean through which used needles can be fed into the container 10 for nonreturnable passage therefrom. A tubular extension 44 projects from the top 6 of the container 10 to provide an inlet 4, and projects internally thereof as shown to provide the non-returnability of used needles fed into the container. The aperture means incorporates a valve device (FIGS. 3A and 3B) formed by a circular aperture 22 being provided in top plate 20 and a plate 24 constrained to move horizontally parallelly to the plate 20 between two extreme positions to respectively close off the aperture 22 in the top plate 20 and to open the aperture 22. The plate 24 has an aperture 26 alignable with aperture 22 of the top plate 20 when the plate 24 is in the open position. Aperture 26 is circular. Both apertures 22 and 26 are provided with a series of serrations 62, 62A as shown around opposed semi-circular parts thereof to form a complete circle of serrations. The plate 24 is spring-biased to the closed position. The plate 24 forms the top of a trigger of a trigger mechanism 28 which is constrained to move in the head unit 12 between inner and outer positions as shown in FIGS. 5 and 6 respectively. The extent of movement of the trigger is determined by slot 8 (FIG. 3B) in plate 24, and a corresponding slot in a bottom plate 24A of the trigger, the slots being engaged by a pin 58 (FIGS. 5 and 6) secured in the head unit 12 between top plate 20 and a bottom plate 20A. The trigger mechanism 28 includes a helical spring 48 mounted therebetween the inner wall of the head unit 12 and the inner wall of the trigger as shown. The spring 48 which forms the spring-biasing of plate 24 and movement of the plate 24 against its biasing is controlled by the trigger mechanism 28. As shown, the head unit is formed in two parts with a first part having the two spaced plates 20, 20A in which aligned apertures 22, 22A are respectively provided, and the second part being the trigger mechanism 28 movable between the two spaced plates 20, 20A and having a passageway 28A alignable with the aligned apertures 22, 22A. The trigger mechanism 28 has two plates 24, 24A in sliding relationship with the spaced plates 20, 20A respectively and between which two plates 24, 24A, the passageway extends. The two plates 24, 24A have apertures 26, 26A.

Figure 2:
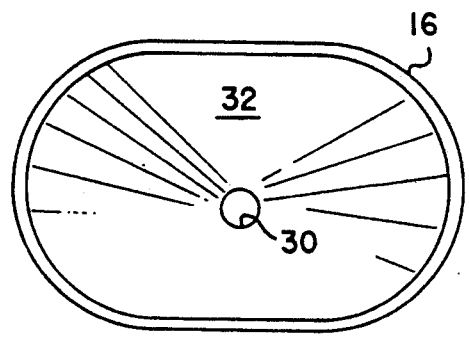
FIG. 2 is a plan view of FIG. 1.
Figure 3A:
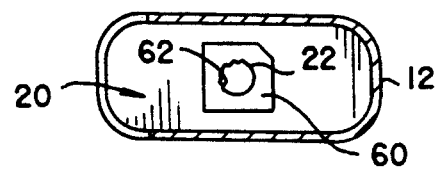
FIGS. 3A and 3B are plan views respectively of a head unit of the system and of a top plate of a trigger mechanism.
Figure 3B:
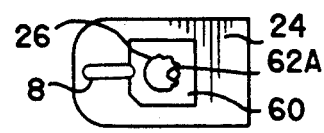

A first cap 16, shaped as shown in FIG. 2, is securable over the head unit 12 with an aperture 30 alignable with aperture 22 in the aperture means, the cap 16 having an inverted skirt 32 extending outwardly and upwardly to act as a protective shroud to protect a hand when holding the assembly during a needle inserting operation. The cap 16 has a groove 16A around the lateral sides of the bottom as shown in FIG. 4 to secure the cap 16 and the head unit 12 together.

The container 10 is commonly called a 'shapes box' and is of a material, such as a synthetic plastics material, resistant to passage therethrough of a needle and is for disposal when full, while the head unit 12 is reusable and of a material capable of being autoclaved for sterilization. In FIG. 1, there is shown in broken line the level 50 at which the container 12 is to be considered full. The container 12 is preferably of a transparent material so as to ascertain when the container 12 is full.

Figure 10:
FIG. 10 is a cross-sectional view of a second cap of the system according to either embodiments.

A second cap 36 shown in FIG. 10 and in the form of a closure is provided with an internal screw-thread to be securable over the neck 14 of the container 10 after the head unit 12 is removed.

The apertures 22, 26 are provided in metal plates 60 inset into complementarily shaped rebates formed in plates 20, 24.

In use, the assembly is held in one hand and a syringe 34 with needle 18 to be removed is held in the other hand. The trigger mechanism 28 is pressed to move plate 24 until its apertures 26 aligns with aperture 22 and the needle is then inserted the aligned apertures 22, 26 until the hub of the needle 18 is located below the plate 24. The trigger is released such that the nozzle of the syringe above the hub is clamped by the serrated edges of the two apertures 22, 26. By pulling or unscrewing the syringe 34 out of the assembly, the needle is released by the hub being prevented from outward movement by its contact under the plates 20, 24. The needle 18 then falls into the container 10. In like manner, other needles 18 can be disposed of into the container 10 until it is full or at the end of a particular time period of use of the syringe, at which time the container 10 can be detached from the head unit 12, a second cap 36 fitted thereto, and disposed of to waste. In the case where the needle being used is a multi-use needle ie. multi-use on the same patient, there is normally a sheath 54 provided. In this case, the sheath 54 can be clamped by the serrations on the apertures 22 26 the assembly left on a surface 52 as shown in FIG. 7, and the needle 18 inserted into the sheath 54 between uses. After finishing using the syringe 34 on the patient, the needle 18 can be fully located in the sheath 54, the assembly lifted, the trigger pressed to release the sheath 54 and allow the sheath 54 and needle 18 to pass further into the container 10 and the sheath and needle detached in the same manner as hereinabove described and deposited into the container 10.

In such use, it is preferred that the oblong skirt 32 have one side with a steeper incline than an opposite side as shown by FIGS. 4 and 7 of the drawings.

In a first modification, the aperture 26 may have a straight knife edge in place of the serrations and be used to guillotine off the needles from their roots in the respective hubs. This modification may be beneficial to people suffering from diabetes who have to inject themselves periodically and then have the problem of having to dispose of the used needles.

In a second modification, other means for securing the first cap 16, head unit 12 and container 10 can be used, such as moulded press stud fastenings.

Figure 8:
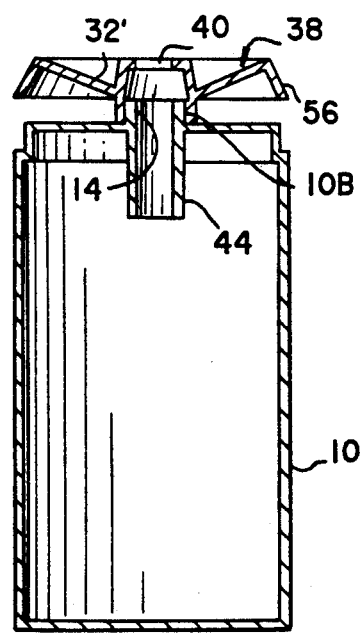
FIG. 8 is a vertical cross-sectional view of a simpler embodiment of the needle disposal system.
Figure 9:
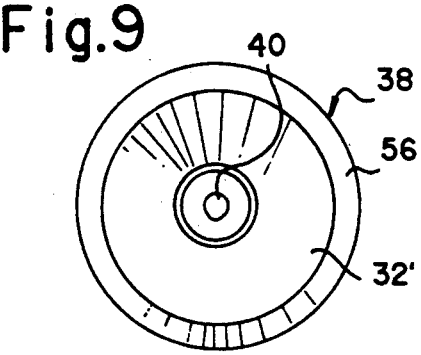
FIG. 9 is a plan view of FIG. 8.

In a second simpler embodiment as shown in FIGS. 8 and 9, in which like numerals are used for like parts, the container 10 has a first cap 38, circular in plan, and having an aperture 40 centrally of its top face, the aperture being of a pear drop shape to allow passage therethrough of a needle and, including a width restriction whereby the top of the hub of a needle 18 can be engaged under the sides defining said restriction and by pulling outwardly, the needle 18 can be detached from a syringe 34. The first cap 38 is securable in screw-threaded engagement with the screw thread 10B and has an inverted skirt 32'. A peripheral flange 56 is provided extending from the outer edge of the skirt 32' of the first cap 16 in an outwardly and downwardly manner a distance substantially the same as the depth of the skirt 32'.

The assembly is sued in much the same manner as described above in the preferred embodiment and is intended for use only for single use needles and when it is to be disposed of the first cap 16' is unscrewed and a cap 36 screwed onto the container. The container when closed by cap 36, and first cap 38 are all intended to be disposed of to waste.

Other variations and modifications can be made without departing from the scope of the invention.

We claim:
1. A needle disposal system comprising: p1 an assembly to e hand held, the assembly having at least two sequentially-arranged components in the form of
   a first cap having an aperture; and
   a head unit having a passage extending therethrough, the head unit being formed as a cylinder and having
   top and bottom spaced plates in which aligned apertures are respectively provided to define the passage and
   a trigger mechanism movable between the top and bottom spaced plates and said trigger mechanism having a passageway alignable with the aligned apertures, the aperture of the first cap and the aligned apertures of the head unit being in alignment when assembled together, the passageway of the trigger mechanism being biased to a first position out-of-alignment with said aperture of the first cap and aligned apertures of the head unit and movable to a position in alignment with said aperture of the first cap and aligned apertures of the head unit.

2. A needle disposal system according to claim 1, wherein the trigger mechanism is spring-biased.

3. A needle disposal system according to claim 2, further comprising a valve device formed by the aperture in the top plate of the head unit, and an aperture formed in an upper plate of two spaced plates of the trigger mechanism.

4. A needle disposal system according to claim 3, wherein the apertures forming the valve device are provided with a series of serrations around opposed semi-circular parts thereof.

5. A needle disposal system according to claim 4, wherein said apertures forming the valve device are provided in metal plates and said metal plates are received in rebates formed in the top plate and the upper plate.

6. A needle disposal system according to claim 2, wherein the trigger mechanism has two plates in sliding relationship with said top and bottom spaced plates respectively and between which top and bottom spaced plates the passageway extends.

7. A needle disposal system according to claim 1 or 2, wherein an extent of movement of the trigger mechanism is determined by slots in the trigger mechanism and a stationary pin which extends through said slots and is anchored in the top and bottom spaced plates.

8. A needle disposal system according to claim 1, further comprising a disposable closed container removably connected to said head unit for holding a plurality of used needles and having an inlet provided in a top end thereof, the inlet being alignable with the aperture of the first cap and the aligned apertures of the head unit wherein upon movement of the passageway into said position in alignment with said aperture of the first cap and aligned apertures of the head unit, a needle can be inserted into the aperture of the first cap to pass through the head unit and into the container, the container having prevention means to prevent a return of said needle through the inlet.

9. A needle disposal system according to claim 1 or 8, wherein the first cap has an inverted skirt extending outwardly and upwardly beyond sides of the head unit to act as a protective shroud to protect a hand when holding the head unit of said assembly during a needle inserting operation.

10. A needle disposal system according to claim 9, wherein the inverted skirt is oblong in plan view and has one longitudinal side with a steeper incline than an opposite longitudinal side.

11. A needle disposal system according to claim 8, wherein the first cap, the head unit and the container have co-operating connection means between adjoining parts thereof.

12. A needle disposal system according to claim 8, wherein a second cap in a form of a closure is provided to be secured over a top of said container inlet after use and prior to disposal.

13. A needle disposal system according to claim 8, wherein the container is formed of a material resistant to passage therethrough of a needle.

14. A needle disposal system according to claim 8, wherein the prevention means is a tubular extension projecting inwardly from around the inlet of the container.

15. A needle disposal system according to claim 14, wherein the container is unitary.

16. A needle disposal system according to claim 1, wherein the head unit and the first cap are reusable and formed of a material capable of being autoclaved.

17. A needle disposal system according to claim 15, 13 or 16, wherein the first cap, the head unit and the container are formed of a plastic material.

* * * * *

UNITED STATES PATENT AND TRADEMARK OFFICE
CERTIFICATE OF CORRECTION

PATENT NO. : 5,187,850
DATED : February 23, 1993
INVENTOR(S) : John W. McCAMMON et al It is certified that error appears in the above-identified patent and that said Letters Patent is hereby corrected as shown below:

On column 4,       Claim 1 as follows:

Line 1, delete "p1".

Line 2, delete "e" and substitute therefor -- be --.

Signed and Sealed this

Third Day of May, 1994

Attest:

BRUCE LEHMAN

Attesting Officer      Commissioner of Patents and Trademarks